US008785610B2

(12) United States Patent
Kilian et al.

(10) Patent No.: US 8,785,610 B2
(45) Date of Patent: Jul. 22, 2014

(54) ALGAL DESATURASES

(71) Applicants: Oliver Kilian, Alameda, CA (US); Bertrand Vick, Berkeley, CA (US)

(72) Inventors: Oliver Kilian, Alameda, CA (US); Bertrand Vick, Berkeley, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/888,310

(22) Filed: May 6, 2013

(65) Prior Publication Data

US 2013/0281683 A1 Oct. 24, 2013

Related U.S. Application Data

(63) Continuation of application No. 13/458,914, filed on Apr. 27, 2012, now Pat. No. 8,440,805.

(60) Provisional application No. 61/480,353, filed on Apr. 28, 2011.

(51) Int. Cl.
*C07H 21/04* (2006.01)

(52) U.S. Cl.
USPC .......................................................... 536/23.2

(58) Field of Classification Search
USPC ....................................... 536/23.2; 435/320.1
See application file for complete search history.

(56) References Cited

U.S. PATENT DOCUMENTS

| | | | |
|---|---|---|---|
| 1,926,780 | A | 9/1933 | Lippincott |
| 3,468,057 | A | 9/1969 | Buisson et al. |
| 3,962,466 | A | 6/1976 | Nakabayashi |
| 4,003,337 | A | 1/1977 | Moore |
| 4,267,038 | A | 5/1981 | Thompson |
| 4,365,938 | A | 12/1982 | Warinner |
| 4,535,060 | A | 8/1985 | Comai |
| 4,658,757 | A | 4/1987 | Cook |
| 5,105,085 | A | 4/1992 | McGuire et al. |
| 5,478,208 | A | 12/1995 | Kasai et al. |
| 5,527,456 | A | 6/1996 | Jensen |
| 5,661,017 | A | 8/1997 | Dunahay et al. |
| 5,668,298 | A | 9/1997 | Waldron |
| 5,723,595 | A | 3/1998 | Thompson et al. |
| 5,823,781 | A | 10/1998 | Hitchcock et al. |
| 6,027,900 | A | 2/2000 | Allnutt et al. |
| 6,117,313 | A | 9/2000 | Goldman et al. |
| 6,143,562 | A | 11/2000 | Trulson et al. |
| 6,166,231 | A | 12/2000 | Hoeksema |
| 6,297,054 | B1 | 10/2001 | Maliga et al. |
| 6,372,460 | B1 | 4/2002 | Gladue et al. |
| 6,448,055 | B1 | 9/2002 | Shimizu et al. |
| 6,736,572 | B2 | 5/2004 | Geraghty |
| 6,750,048 | B2 | 6/2004 | Ruecker et al. |
| 6,831,040 | B1 | 12/2004 | Unkefer et al. |
| 6,871,195 | B2 | 3/2005 | Ryan et al. |
| 7,244,609 | B2 | 7/2007 | Drocourt et al. |
| 7,381,326 | B2 | 6/2008 | Haddas |
| 7,410,637 | B2 | 8/2008 | Sayre et al. |
| 7,449,568 | B2 | 11/2008 | Fukuda et al. |
| 7,547,551 | B2 | 6/2009 | Schuler et al. |
| 8,039,230 | B2 | 10/2011 | Otte et al. |
| 8,119,859 | B2 | 2/2012 | Vick et al. |
| 8,314,228 | B2 | 11/2012 | Kilian et al. |
| 8,318,482 | B2 | 11/2012 | Vick et al. |
| 2003/0049720 | A1 | 3/2003 | Hoshino et al. |
| 2003/0140021 | A1 | 7/2003 | Ryan et al. |
| 2003/0143743 | A1 | 7/2003 | Schuler et al. |
| 2003/0199490 | A1 | 10/2003 | Antoni-Zimmermann et al. |
| 2003/0211089 | A1 | 11/2003 | Sayre et al. |
| 2004/0161364 | A1 | 8/2004 | Carlson |
| 2004/0262219 | A1 | 12/2004 | Jensen |
| 2005/0064577 | A1 | 3/2005 | Berzin |
| 2005/0095569 | A1 | 5/2005 | Franklin |
| 2005/0124010 | A1 | 6/2005 | Short et al. |
| 2005/0170479 | A1 | 8/2005 | Weaver et al. |
| 2005/0181345 | A1 | 8/2005 | Bradbury et al. |
| 2005/0260553 | A1 | 11/2005 | Berzin |
| 2006/0031087 | A1 | 2/2006 | Fox et al. |
| 2006/0044259 | A1 | 3/2006 | Hotelling et al. |
| 2006/0045750 | A1 | 3/2006 | Stiles |
| 2006/0101535 | A1 | 5/2006 | Forster et al. |
| 2006/0122410 | A1 | 6/2006 | Fichtali et al. |
| 2006/0155558 | A1 | 7/2006 | Corpening |
| 2006/0166243 | A1 | 7/2006 | Su et al. |
| 2006/0166343 | A1 | 7/2006 | Hankamer et al. |
| 2006/0192690 | A1 | 8/2006 | Philipp |
| 2007/0178451 | A1 | 8/2007 | Deng et al. |
| 2008/0118964 | A1 | 5/2008 | Huntley et al. |
| 2008/0120749 | A1 | 5/2008 | Melis et al. |
| 2008/0160488 | A1 | 7/2008 | Younkes et al. |
| 2008/0160591 | A1 | 7/2008 | Willson et al. |

(Continued)

FOREIGN PATENT DOCUMENTS

| | | |
|---|---|---|
| CN | 1627764 | 6/2005 |
| CN | 1867140 | 11/2006 |

(Continued)

OTHER PUBLICATIONS

Santin-Montanya, I. "Optimal Growth of *Dunaliella primolecta* in Axenic Conditions to Assay Herbicides," Chemosphere, 66, Elsevier 2006, p. 1315-1322.
Felix, R. Use of the cell wall-less alga *Dunaliella bioculata* in herbicide screening tests, Annals of Applied Biology, 113, 1988, pp. 55-60.
Janssen, M. "Phytosynthetic efficiency of *Dunaliella tertiolecta* under short light/dark cycles," Enzyme and Microbial Technology, 29, 2001, p. 298-305.
Saenz, M.E., "Effects of Technical Grade and a Commercial Formulation of Glyphosate on Algal Population Growth," Bulletin of Environmental Contamination Toxicology, 1997, 59: pates 638-644.
Christy et al., "Effects of Glyphosate on Growth of *Chlorella*," Weed Science, vol. 29, Issue 1, Jan. 1981, pp. 5-7.

(Continued)

*Primary Examiner* — Maryam Monshipouri
(74) *Attorney, Agent, or Firm* — Carr & Ferrell LLP

(57) ABSTRACT

Provided herein are exemplary isolated nucleotide sequences encoding polypeptides having desaturase activity, which utilize fatty acids as substrates.

8 Claims, 11 Drawing Sheets

(56) References Cited

U.S. PATENT DOCUMENTS

| | | | |
|---|---|---|---|
| 2008/0194029 | A1 | 8/2008 | Hegemann et al. |
| 2008/0268539 | A1 | 10/2008 | Singh et al. |
| 2008/0293132 | A1 | 11/2008 | Goldman et al. |
| 2009/0029445 | A1 | 1/2009 | Eckelberry et al. |
| 2009/0061493 | A1 | 3/2009 | Trimbur et al. |
| 2009/0061928 | A1 | 3/2009 | Lee et al. |
| 2009/0148931 | A1 | 6/2009 | Wilkerson et al. |
| 2009/0234146 | A1 | 9/2009 | Cooney et al. |
| 2009/0317857 | A1 | 12/2009 | Vick et al. |
| 2009/0317878 | A1 | 12/2009 | Champagne et al. |
| 2009/0317904 | A1 | 12/2009 | Vick et al. |
| 2009/0319338 | A1 | 12/2009 | Parks et al. |
| 2009/0325270 | A1 | 12/2009 | Vick et al. |
| 2010/0068772 | A1 | 3/2010 | Downey |
| 2010/0100520 | A1 | 4/2010 | Dargue et al. |
| 2010/0198659 | A1 | 8/2010 | Meltzer et al. |
| 2010/0210003 | A1 | 8/2010 | King et al. |
| 2010/0210832 | A1 | 8/2010 | Kilian et al. |
| 2010/0314324 | A1 | 12/2010 | Rice et al. |
| 2010/0323387 | A1 | 12/2010 | Bailey et al. |
| 2010/0330643 | A1 | 12/2010 | Kilian et al. |
| 2011/0015415 | A1 | 1/2011 | Singh et al. |
| 2011/0059495 | A1 | 3/2011 | Bailey et al. |
| 2011/0091977 | A1 | 4/2011 | Kilian et al. |
| 2012/0190115 | A1 | 7/2012 | Kilian et al. |
| 2013/0102040 | A1 | 4/2013 | Radakovits et al. |
| 2013/0131330 | A1 | 5/2013 | Kilian et al. |

FOREIGN PATENT DOCUMENTS

| | | | |
|---|---|---|---|
| CN | 1956335 | | 5/2007 |
| CN | 101289659 | * | 6/2008 |
| CN | 101289659 | | 10/2008 |
| WO | 2004106238 | A2 | 12/2004 |
| WO | 2007084078 | | 7/2007 |
| WO | 2008060571 | A2 | 5/2008 |
| WO | 2008106803 | A1 | 9/2008 |
| WO | 2009124070 | A1 | 10/2009 |
| WO | 2009149470 | A1 | 12/2009 |
| WO | 2010011335 | A1 | 1/2010 |
| WO | 2011011463 | A2 | 1/2011 |
| WO | 2011049995 | A1 | 4/2011 |

OTHER PUBLICATIONS

Roessler et al., "Genetic Engineering Approaches for Enhanced Production of Biodiesel Fuel from Microalgae," ACS Symposium Series; American Chemical Society, 1994, pp. 255-270.

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601, 1988.

Hallmann et al., "Genetic Engineering of the Multicellular Green Alga *Volvox*: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of *Chlamydomonas* Using the *Chlamydomonas* Gene for Nitrate Reductase" The Journal of Cell Biology 109 (6, part 1): 2589-2601, 1989.

Prein et al. "A Novel Strategy for Constructing N-Terminal Chromosomal Fusions to Green Fluorescent Protein in the Yeast *Saccharomyces cerevisiae*" FEBS Letters 485 (2000) 29-34.

Schiedlmeier et al., "Nuclear Transformation of *Volvox carteri*" Proceedings of the National Academy of Sciences USA 91(11): 5080-5084 (May 1994).

Wendland et al. "PCR—Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla *Chlamydomonas reinhardtii*," Plant Jour. ePub Jan. 17, 2009, vol. 58, No. 1, pp. 157-164 (Abstract Only).

Chen et al., "Conditional Production of a Functional Fish Growth Hormone in the Transgenic Line of *Nannochloropsis oculata* (Eustigmatophyceae)," J. Phycol. Jun. 2008, vol. 44, No. 3, pp. 768-776.

Nelson et al., "Targeted Disruption of NIT8 Gene in *Chlamydomonas reinhardtii*." Mol. Cell. Bio. Oct. 1995, vol. 15, No. 10, pp. 5762-5769.

Kureshy et al., "Effect of Ozone Treatment on Cultures of *Nannochloropsis oculata, Isochrysis galbana,* and *Chaetoceros gracilis*," Journal of the World Aquaculture Society, 1999, 30(4), pp. 473-480.

Genbank Accession No. U71602 (*Nannochloropsis* sp. Violaxanthing/chlorophyll a binding protein precursor (NANVCP) mRNA, 1996.

Sukenik et al. "Characterization of a Gene Encoding the Light-Harvesting Violaxanthin-Chlorophyll Protein of *Nannochloropsis* Sp. (Eustigmatophyceae)," Journal of Phycology, Jun. 2000; 36(3), pp. 563-570.

Abe et al., AG610981, *Musmusculus* molossinus DNA, 2004.

Kopczynski et al., CO268749, *Drosophila melanogaster* cDNA clone EK092604, 2004.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis* Sp. In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga *Nannochloropsis oculata* (eustigmatophyceae)," Journal of Phycol, vol. 44, pp. 99-102, 2008.

Thiel et al., "Transformation of a Filamentous Cyanobacterium by Electroporation," Journal of Bacteriology, Oct. 1989, vol. 171, No. 10, pp. 5743-5746.

Krienitz et al., "*Nannochloropsis limnetica* (Eustigmatophyceae), a new species of picoplankton from freshwater," Phycologia, 2000, vol. 39, No. 3, Abstract.

Lee et al., "Isolation and Characterization of a Xanthophyll Aberrant Mutant of the Green Alga *Nannochloropsis oculata*," Marine Biotechnology, 2006, vol. 8, pp. 238-245.

Sukenik et al., "Regulation of Fatty Acid Composition by Irradiance Level in the Eustigmatophyte *Nannochloropsis*," Journal of Phycol., 1989, vol. 25, pp. 686-692.

Rocha et al., "Growth Aspects of the Marine Microalga *Nannochlorpsis gaditana*," Biomolecular Engineering, 2003, vol. 20, pp. 237-242.

MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.

Dunahay et al, "Manipulation of Microalgal Lipid Production Using Genetic Engineering," Applied Biochemistry and Biotechnology, 1996, vol. 57/58/.

Witkowski et al., "Conversion of a B-Ketoacyl Synthase to a Malonyl Decarboxylase by Replacement of the Active-Site Cysteine with Glutamine," Biochemistry, 1999, vol. 38, 11643-11650.

Kisselev, "Polypeptide Release Factors in Prokaryotes and Eukaryotes: Same Function, Different Structure," Structure, vol. 10, Jan. 2002.

Whisstock et al., "Predication of protein function from protein sequence and structure," Q. Rev. Biophysics, 2003, vol. 36, pp. 307-340.

Broun et al., "Catalytic Plasticity of Fatty Acid Modification Enzymes Underlying Chemical Diversity of Plant Lipids," Science, vol. 282, 1998.

Wishart et al., "A Single Mutation Converts a Novel Phosphotyrosine Binding Domain into a Dual-specificity Phosphatase," J. Biol. Chem. 1995, vol. 270(45), pp. 26782-26785.

Geng et al, "Construction of a System for the Stable Expression of Foreign Genes in *Dunaliella salina*," Acta Botanica Sinica 46(3): 342-346, 2004.

Chen et al., "Highly Efficient Expression of Rabbit Neutrophil Peptide-1 gene in *Chlorella* Ellipsoidea Cells," Current Genetics 39(5-6): 365-370, 2001.

(56) References Cited

OTHER PUBLICATIONS

Suga et al., "Control by Osmolarity and Electric Field Strength of Electro-Induced Gene Transfer and Protein Release in Fission Yeast Cells," Journal of Electrostatics 64(12): 796-801, 2006.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)—Communications and Administration Office, Apr. 2008.
Department of Environment, Housing and Territorial Development Ministry, Resolution (1009), published Jun. 17, 2008.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25, 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.
Kilian et al., "High-efficiency homologous recombination in the oil-producing alga *Nannochloropsis* sp.," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of *Chlamydomonas reinhardtll*," Created Dec. 2003, [online, retrieved Oct. 14, 2010] <http://etd.lsu.edu/docs/available/etd-0828103-114026/unrestricted/Pollock_dis.pdf>.
DROCOURT: GenBank Accession No. X52869.1, created Jan. 3, 1995.
PAN: GenBank Accession No. EE109892.1, created Jun. 23, 2008.
PAN: GenBank Accession No. EE109907, created Jun. 23, 2008.
Henriquez et al.: GenBank Accession No. Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of *Nannochloropsis oculata* (Eustigmatophyceae)," Chinese Journal of Oceanology and Limnology, vol. 28, No. 4, pp. 802-807, 2010.
Lumbreras et al., "Efficient Foreign Gene Expression in *Chlamydomonas reinhardtii* Mediated by an Endogenous Intron," The Plant Journal, vol. 14, No. 4 Jan. 1, 1998, pp. 441-447, XP001150496, ISSN: 0960-7412, DOI: 10.1046/j.1365-313X.1998.00145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in *Arabidopsis*," The Plant Journal, vol. 40, No. 5, Dec. 1, 2004, pp. 744-751, XP55029911, ISSN: 0960-7412, DOI:10.1111/j.1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.
Examination Report mailed Feb. 20, 2013 in Australian Application No. 2009274500 filed Jul. 24, 2009.
Second Office Action mailed Mar. 5, 2013 in Mexican Application No. MX/a/2011/000934 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.X filed Jul. 24, 2009.

* cited by examiner

| Desaturase No. | SEQ ID NO | Desaturase Type | Times Up Regulated in Presence/Absence Nitrogen | Substrate 1 | Product 1 | Substrate 2 | Product 2 | Gene Regulation in Mutant Up/Down | Substrate 1 to Product 1 Conversion | Gene Regulation in Mutant Up/Down | Substrate 2 to Product 2 Conversion |
|---|---|---|---|---|---|---|---|---|---|---|---|
| 3 | 1 | Delta 12 Desaturase | 1.5X/Absence | Palmitolenic acid (16:2(n-7)) | 6,9,12-hexadecatrienoic acid (16:3(n-4)) | Oleic acid, cis-9-octadecenoic acid (18:1(n-9)) | Linoleic acid, all-cis-9, 12-octadecadienoic acid (18:2(n-6)) | Up | Increase product 1 by 85% | Up | Increase product 1 by 50% |
| 5 | 2 | Delta 12 Desaturase | Not Regulated | Oleic acid, cis-9-octadecenoic acid (18:1(n-9)) | 12-octadecadienoic acid (18:2(n-6)) | | | Down | Increase of substrate 1 by 100% | | |
| 7 | 3 | Omega 3 Desaturase | 4X/Presence | Arachidonic acid, all-cis-5,8,11,14-eicosatetraenoic acid (20:4(n-6)) | Eicosapentaenoic acid, all-cis-5,8,11,14,17-eicosapentaenoic acid (20:5(n−3)) | Linoleic acid, all-cis-9, 12-octadecadienoic acid (18:2(n-6)) | α-Linolenic acid, all-cis-9,12,15-octadecatrienoic acid (18:3(n−3)) | Up | Decrease of subtrate 1 by 60%, EPA:ARA ratio changes from 7.5 to 22; a ~200% increase | Up | Increase of product 2 by 650%; 18:3n3 to 18:2n6 ratio changes from 2.5 to 15.8 (550% increase) |
| 9 | 4 | Delta 9 Desaturase | 6.6X/Absence | Palmitic acid, or hexadecanoic acid (16:0) | Palmitoleic acid, cis-9-hexadecenoic acid (16:1(n-7)) | | | Up | Increase of product 1 by 25%; increase of 16:1n7 to 16:0 ratio from 0.48 to 0.6; a 25 % increase | | |
| 10 | 5 | Delta 9 Desaturase | 5X/Absence | Palmitic acid, or hexadecanoic acid (16:0) | Palmitoleic acid, cis-9-hexadecenoic acid (16:1(n-7)) | | | Up | Increase of product 1 by 34%; increase of 16:1n7 to 16:0 ratio from 1.02 to 1.19; a 16% increase | | |

FIG. 1

ATGGGACGCGGTGGCGAGCGGGTCGAGACGACGGAGTCTTTGAGCTTCACGGCCGACAAGGCGGGGACCATCAAGCAGCGTGGGGGGAAGATCACATGGG
ATGAGGTATGTGACGGGGCATGGAGGCGTCGGACGGAGGAATGCAGGGAGAAAGGGAAAGAGAGGAGAAAGGAAAGCAAGGTGTATCTGCTGTGGCGGT
AGATTTGCCATCTATATGATCCTTTGAGTGCAGTGCTTGGATGGAAGGCGTCAGTGCAATCCTGTATGTGATGACGGAGGAAGCAGCACACCTTCCCTTCCCTA
ATCTCTGTCCCCTACAACCCCGCGTATCCTCTTCTCCCGATCACCCACGCTCACACACACCTATTTACTCTCCAGGTGCGTCAGCACAAGACGCCTCAGGACGCTT
GGCTCGTGTATAGGAATAAGGTCTACGACGTGTCGGGCTGGCAAGATCACCCCGGGGGGAACGTCATCTTCACTCACGCCGGCGGGGACTGCACGGATATTT
TCGCGGCGTTCCACCCTCTTGGCGCCACCTCTTATCTTGATCCATTTTACATTGGCGAGCTGGAGCCGGGCTCGGACAAGAAGCCCGCAGCGCAGGCGAACTTT
GAGCGGGCCTACAGGGATCTCAGGGGGAAGCTTATCGCGGGTGGGTTTTTCAAGGCGAATCCTTTGTACTATGTCTGGAAGGTAGTATCGACAGTTGCCCTTG
CTGTAGGTGCGTGGATGCTGGTGGCTTGGTCGCAGAACCTGGGCGTGCAGATGCTGTCTGCGTTTTTGGTGGCTCTGTTCTGGCAGCAATGTGGCTGGTTGGC
CCATGACTTCCTGCACCACCAGGTATTTAAGAACCGTGCGTTGGGTGACCTGGCCGGCATCGTTATCGGCAATGTCTTCCAGGGTTTCTCCGTGGCATGGTGGA
AGAACAAGCATAACACTCACCACGCGGTGCCCAACCTCGTCGAGTCCTCTCCGGACGCGCAAGACGGAGACCCTGACATTGACACCATGCCCATACTGGCCTG
GTCGCTCAAGATGGCCGACAGGGCGCAGCAATACTCATGGGGACCCTTCTTTGTCAGGCATCAGTCGCTGCTATACTTCCCCATCCTGCTCGTGGCGCGGATTT
CATGGTTGATGCAGTCGTTCTTGTTTGTCTTTGACTCCGTCCCTGGAGCGAGTCTGTGGGCAACCAAGGGCGCGACGGCTGAGAGACAGGCGATCAAGAATGT
CGGGTTGGAGAAGGTGGGGCTGGTTGCGCACTACCTGTGGTACGGTGCGCTGATGCTGTGCCACATGTCCCTGGCCCGCGCCCTGCTGTACTTCCTGGCGAGC
CAGATGATGTGCGGGTTCTTGCTCGCGCTTGTTTTCGGGCTTGGGCACAACGGCATGGCTGTTTACGACGCGGACGCCCGGCCCGACTTCTGGAAGCTGCAGG
TGACGACGACGAGGAACGTGACGGGCTCGTGGTTGGTGCAGTGGTTCTGTGGCGGCCTCGGCTACCAGGTGGACCACCACCTGTTCCCCATGATCCCGCGGC
ACCGCCTAGGGAAGCTCCACGGGCTCGTGGAGGGTTTCTGCAAGGATCACGGGGTGAAGTACCACGAGACGAATATGTGGGAGGGGACCAAAGAGGTGTTG
GCTCACTTGAGCAGTGTGACGAAAGAGTTCGTGGCCGATTTCCCCGCCATGTAA

FIG. 2

ATGGGACGCGGCGGTGAGAAGACGGTGACCCCTCTTCGCAAAAAAACCCTCCTGGATGCCGCTTCCACGATCAGCGGCACAGTCAGACCAAGCAAGGC
AGTAGAGGCCCTGCCCACGGAGGAGCTGCGTAAGAAGGCCGCACAATACGGTATCAACACTTCGGTCGACCGCGAAACACTGCTGAGGGAGCTGGTAA
GTGCTTGTGATCGCTTGAGGGGTGGATGGGTAAAAACAGTTCCCTCCCATTCGTGCATGTGGTCAGACGGATATAAGAATTACGTGCCATGCCCTTGACA
TTTTGATGTCACCGCGCTGTCTTCACTTCCCGCTCCAATAGCTATTATGTACGTGGACTGGCGGCTGCTGCCCCTTGTCCTTTTTTCTTCCCTCCCTTGCATG
CCACCTAAGCATACCTCGCTCATTCACTTTCCGCATGTCATCATAACCACAGGCTCCCTACGGCGATATCCTCCTCCGCAATGACGCCCCTAAATCCCTGCC
CCTTGCCCCTCCTCCTTTCACCCTCTCCGACATCAAGAACGCTGTTCCCCGTCACTGCTTTGAGCGTTCCCTCTCCACCTCCCTCTTCCACTTGACCATCGACT
TGATCCAAGTCGCTGTCCTCGGGTACCTTGCCTCATTACTGGGCCACTCCGACGTCCCGCCCATGTCTCGTTATATTCTATGGCCGTTGTACTGGTACGCGC
AAGGCTCTGTGCTGACGGGAGTGTGGGTCATTGCCCACGAGTGCGGGCACCAATCGTTTTCGCCTTACGAGAGCGTGAACAACTTCTTTGGGTGGCTCTT
GCACTCGGCCTTGCTTGTGCCCTATCACTCTTGGAGGATTTCCCATGGAAAGCACCACAACAACACGGGGAGCTGCGAGAATGACGAGGTCTTTGCGCCG
CCTATTAAGGAGGAACTGATGGACGAGATTTTGCTTCACTCCCCTTTGGCGAATCTGGTGCAGATAATCATAATGTTGACCATCGGATGGATGCCGGGGT
ACCTGCTCCTGAACGCTACGGGGCCTAGGAAATACAAGGGACTGAGCAATAGCCACTTTAACCCAAATTCGGCGTTGTTTTCTCCGAAGGACCGTCTGGA
CATTATTTGGTCCGACATTGGGTTTTTCGTGGCCTTGGCCTGCGTGGTATATGCCTGTGTGCAGTTTGGATTTCAAACGGTGGGAAAGTATTACCTGCTGC
CGTACATGGTGGTCAATTATCACCTGGTCCTCATCACGTACCTGCAGCACACGGACGTCTTCATCCCCCACTTTCGGGGGAGCGAGTGGACGTGGTTTAG
GGGCGCCCTTTGCACGGTCGACCGATCCTTCGGCTGGCTTTTGGACCATACGTTTCACCATATCAGTGACACTCATGTGTGCCACCACATCTTCAGCAAGA
TGCCGTTCTACCACGCGCAGGAGGCGAGTGAGCACATTCGCAAGGCGTTGGGCGACTATTATTTGAAGGATGATACCCCGATTTGGAAGGCATTGTGGC
GAAGTTATACCCTGTGCAAGTACGTGGACTCGGAGGAGACGACGGTATTCTACAAGCAGCGGGCATAG

FIG. 3

ATGGTTGAGCAAACGTTACCGACCTTGTCCCAGATCAAGAAAGCCATCCCCGAGAAATGCTTCCAGGTACAACGCGGAGGGGG
TGGAGGGGGGGGGAGTGAAGCAGGGGGGGGGGAGAACGGGTGATAAAGAGGGATAGGTTGAGAGAATGGAAGAGGGAA
AAGGGAAGAAGTGTTGCAAGGACGTGGTGTTGCAAGGACGTGGTGTACCTGTGCGTACCCGACCCGCGTGTCCACAAGCTCG
AGCAGTCCGAAGCGCTTTGTCACCCTTCTCACCACATATCCCTCCCTCCTGTCTCCATTTCCTCCCTTCAGAAATCCCTCCTCCGCT
CCTTTTACTACATGCTGAGGGACTTCGCGGCCTTGGCGGCACTCTACTTTGTTTATCCCACAGTGCAGGCCAAGTATGGATTGCC
TGGTTTGTTTGTGTGGTGGAACCTCGCAGGTAGGGAGGGAGGGAGGATGAGAGGGAAGAGAATTGGGGAAAGCCATCGAGC
CGTCTTATACGTCTTCTAGGCACTCACAAACTCTTCTCCCCTCCCTCCTCCCCTTCCTCCCCAGGCTTTTTCATGTGGTGCCTCTTCG
TGATAGGCCACGATTGCGGCCATGGCTCCTTCTCCGAGTACAAGTGGCTCAATGACATATGCGGTCACATTTGCCACGCCCCCTT
GATGGTGCCTTACTGGCCTTGGCAGAAGGTATGGGAGCCAGGCCGCCCTCCCTCCTTCCCTCCCTCCCCCCTTCCCTCGTTTTAAT
GACATGTCGATCATCTCATTCATTCTATCTCTGCCTCCCTTCCTCCCTACCTCCCTCCCTCCATCCCTTTCGCCAGTCCCACCGCCTT
CACCACATGTACCACAACCACCTGACTAAGGACATGTCACACCCGTGGATGACCAAGGAGGTGTTCGAGGTAGGAAGGGAGG
GAGGGCGGATATGTTGTTGGGATGAACGCTATAGAGAAGGCACGGGCTTGTTTGATCCTGTGGCATACCTCACGCCTTCCCTCC
CTCCCTCCCTCCCTCCCTCCCTTTTTTTTCAGGACTTGACCCCATTCGAGCAGGCGTTGCTGGAGAACCCGCTGTCCCTCTTCATCA
AGTACACCTTCCTTTACCTCTTTGCGGGCAAGATGGATGGCAGGTATGAAGAGGGATGAGGGCAGAGGACGGATGAGGGAGA
GGACGGGAAGTCGGACACGGAGTGGGCTCGCTTCTTGTCCCACTCTCGATTGCTCACCCTCCCTCCCTCCCTCCCTCCCTCCCTCC
CTCCCTCCCTTCCGTCTGGACACAGCCATGTAGTTCCATTCTCCCCCCTCTTCACCGACACCAAGGAGCGGGTGCAATGCGCTGT
GTCGACGCTGGGTATGGTCGTCGCAGGCGCCCTTGTGTACATCGGGCTCGAGGGCGGGAAGGAGGGAGGGATGGCGAGGAT
AGGATCCATTTATGTGGTGCCGTTGCTGGTGTTCAATGCCTGGATCACGATGGTGACATACCTGCAGCACCACGATGAGGACAC
CAAGGTTTATGCAGAGGGGGAGTGGAACTACATCAAGGGGGCCCTGGAGACGATCGACCGCGAATACGGCATGGGGATTGAC
GGTGAGTTTATCATTGGTTAAATATATTGTGACAACTCTAATTAATTGATTACTTTCATGTTTTAATTGACAATTCGTTCTCGGTG
ATGGTGAGGACACCAAGGTGACAGTTTCCCACAGCTCTGTCTTAGCCTCAAGACTAAGCTGGCCTCCTTTCCTCCCGCCCTCCCT
TCCCTTAGACCTCTCCCACAATATCACGGATGGCCACGTGGCGCACCACCTCTTCTTCACGCAGATCCCGCACTACCACCTGACG
GCGGCCACGGCCGCTGTGAGACAATGCCTGCAACCTACGGGGACCTACAAGAAGAGGAGGAGCTGGAATTTTCTCGCTCGTTT
CACGGAGCTTAACTACCGTTTGAAATACGTCGCGGGCCAGGGCGTGCTCTCCTATGTGGATTGGGAGGTAAGGGAAGGAGGA
AGAGCGAAGGAGTGAGGGAAAGAGTGAGGAAAAGTAAATATAGATGGAGGGTTTGCGAGCTCAGCTTTCTTCCTTCTCACCCT
TGCTCCCTCCCTCGTCTTGTAACCATCACAGGTCGCTCGCAAGACCCCTGCTTCCGCCGTCACCTCCTCTTTCTCTTCCTCCTCCTC
TTCCTCCCTTCCGGCAGAGGCTGCTGTCAAGGCGGCTGCTGCCGTTCCCGTTGCTGCTGTTGCTGCTCCCGTCCGAGAAGGAAG
ACCAACACGCAAGCGCTCTCCCACCCGTTCATCCTCCCCTCCGTAA

FIG. 4

ATGCACGTCTACCCCGACAAGCACGAAGTCATTGTCAGCATGGAGCCCATGGTGGAAGGGATGCTCTCGAAGCTCCTCCTCCCCACGGGGGAGAAGGCTT
GGCAACCGTCCGACTTTGTCCCGGACCTGACCAAGGAAGGGTGGGAAGACGAGGTAAAGGAATTCAGGGAAAAGGCGGAGACGTTGCCGGACGAGACG
CTGGTGGTCTTGGTGGGGGACATGGTGACTGAGGAGGCGTTGCCCACTTACCAGACGCTGTTGAACACGTTCGAGGGCGTGGATGACCCCACCGGGACG
AGTCCTTCGGCCTGGTGCCGATGGACACGGGGGTGGACGAGCGAGGAGAACAGGCACGGGGATCTGCTCAACCGGTACTTGTACTTGACGGGGCGCGT
GGACATGCGCGCGATCGAGTGCACGATTCAGCACCTGGTACGTGGGGATGGGAGGGAGGGAGAGAGGGAGGGATGGAGGAAGGCTCCTGTTCTTGTGT
TCCCCCCCTTCGTCTCGCGCGATGTCTAACTCATTCTTCCCACCCTCCCTCCCTCTGCGTCCGTAAATTAGATTTCGAGCGGTTTCAACCCCAAAATCAAGAAG
GATCCGTACAAGGGTTTCGTATACACCTCCTTCCAAGAGCGAGCAACCAAGATCTCCCATCAGAATGTGGCGCGGCTGGCCAACAGCGCCGGTGATGGCA
ATCTGGGTCTGATCTGCAGTAAGATTGCAGGGGATGAGTCGAGGCACGAGAAGGCATACCAAGCCATCTTCCAGGAGATCCTCAAGAAGGACCCGGAAG
GGGGGTTGAAGAGCTTCTATGAGTTAATGAGTGATCAGGTAGGGAGGGCGGAGGAGAGGGAGGGGGAAAGGGAGGGAGGTAGGTACGCATTAGGAG
GCAGGAGGAAGGGAACGACACAAGTACTTTCACCATGGGCCAAGATACGGCTGTTTACCTTTCCCTCCTCCCTCCCTCTCTCCCTCCCTCCCTCCCTCCCTCC
CTCATCTCAGATCACCATGCCTGCCGTGATGATGACGGACGGCCACGACCCGGACCTCTTCGAGCACTTCTCGGTCACGGCGCAGAAGCTCGGTGTCTACA
CGGCAGTGGACTACGCCAACATTCTGGAATATTTGGTGGAGACATGGGACATCGAGCACATGGGAGGCCTGTCTTCTGAAGGGGCCAAGTACCAGGAGA
AGCTCTGCAAGCTCGCGCCCCGATACATGAGGCTTGCCGAGATGAGTCTTGACCGGGTGAAAAAGATGCCCAAGACGCCTTATTCTTGGATCCATGGACG
CGTGGCTTAA

FIG. 5

ATGGTCTTCCAGCTCGCCCGAGACTCTGTCTCGGCCCTGGTCTATCATTTCAAAGAAGGAAACCTTAACTGGCCTATGATTATCTACCTCGTC
CTTGTCCACTTGGCGGGCTACATCGGTCTGACTACCATTCTGGCTTGCAAATGGCAAACTCTCCTCGAAGCGTTCATCCTATGGCCCATCACC
GGGCTGGGGATTACTGCCGGCGTACACCGACTTTGGGCACACCGTTCGTACAATGCCACGTTGCCTTATCGCATCCTGTTGATGTTGTTCAA
CTCAATTGCGAACCAAGGCAGCATCTACCACTGGTCCCGGGACCACCGCGTGCACCACAAGTACTCCGAGACTGATGCTGACCCACATAAC
GCCACCCGTGGCTTCTTCTTCGCGCACATGGGCTGGCTCATTGTTAAGAAGCACCCCAAGGTCGTCGAAGGGGGGAAGCAACTCGATTTCT
CCGATTTGGCTGCCGATCCCGTGGTGCGATTCCAGCGTGATTGGGATCCGTGGTTCGCCCAGTTTATGTGCTTTGTCATGCCGGCGCTTGTT
GCATCGAGGTTCTGGGGTGAGGCGTTCTGGAACGCCTTTTGGGTGGCGGGGGCTTTGAGGTATATGTTGGTGCTGCACTTCACCTGGATGG
TTAACAGTGCGGCGCACTTGTATGGCGACCACCCGTACGACCCTACCATGTGGCCGGCGGAGAACCCGTTGGTATCGGTAGTGGCGATCGG
AGAAGGCTGGCATAACTGGCACCATCGTTACCCCTACGACTACGCGGCTTCCGAGTTTGGGATTTCGCAGCAGTTCAACCCGACCAAGGCG
TTCATTGATTTTTTTGCGGCCATAGGGATGGTGACGAACCGAAAACGTGCGACGGGGGCTTGGGCAAAGCTCAAGGAATCCAGGGCAAGG
GATGCGGCGAATGGGAAGAGCATGAAAGATTTCAAGGGAAGAGGCTCGGGGTCAGACTATGGTACGACAAACACCAATTACGCGGTGTC
GAACAAGACAGTGGTGACCGACAAGGGGGCGCAACAACCAGGGTGGGAGGAGAGCAATCACCCCAAGTACAACTAA

FIG. 6

MVRQHKTPQDAWLVYRNKVYDVSGWQDHPGGNVIFTHAGGDCTDIFAAFHPLGATSYLDPFYIGELEPGSDKKPAAQANFERAYRDLRGKLIAGGF
FKANPLYYVWKVVSTVALAVGAWMLVAWSQNLGVQMLSAFLVALFWQQCGWLAHDFLHHQVFKNRALGDLAGIVIGNVFQGFSVAWWKNKH
NTHHAVPNLVESSPDAQDGDPDIDTMPILAWSLKMADRAQQYSWGPFFVRHQSLLYFPILLVARISWLMQSFLFVFDSVPGASLWATKGATAERQA
IKNVGLEKVGLVAHYLWYGALMLCHMSLARALLYFLASQMMCGFLLALVFGLGHNGMAVYDADARPDFWKLQVTTTRNVTGSWLVQWFCGGLG
YQVDHHLFPMIPRHRLGKLHGLVEGFCKDHGVKYHETNMWEGTKEVLAHLSSVTKEFVADFPAM

FIG. 7

MGRGGEKTVTPLRKKTLLDAASTISGTVRPSKAVEALPTEELRKKAAQYGINTSVDRETLLRELAPYGDILLRNDAPKSLPLAPPPFTLSDIKNAVPRHCFERSLST
SLFHLTIDLIQVAVLGYLASLLGHSDVPPMSRYILWPLYWYAQGSVLTGVWVIAHECGHQSFSPYESVNNFFGWLLHSALLVPYHSWRISHGKHHNNTGSCE
NDEVFAPPIKEELMDEILLHSPLANLVQIIIMLTIGWMPGYLLLNATGPRKYKGLSNSHFNPNSALFSPKDRLDIIWSDIGFFVALACVVYACVQFGFQTVGKYY
LLPYMVVNYHLVLITYLQHTDVFIPHFRGSEWTWFRGALCTVDRSFGWLLDHTFHHISDTHVCHHIFSKMPFYHAQEASEHIRKALGDYYLKDDTPIWKALW
RSYTLCKYVDSEETTVFYKQRA

FIG. 8

MVEQTLPTLSQIKKAIPEKCFQKSLLRSFYYMLRDFAALAALYFVYPTVQAKYGLPGLFVWWNLAGFFMWCLFVIGHDCGHGSFSEYKWLNDICGHICHAPLM
VPYWPWQKSHRLHHMYHNHLTKDMSHPWMTKEVFEDLTPFEQALLENPLSLFIKYTFLYLFAGKMDGSHVVPFSPLFTDTKERVQCAVSTLGMVVAGALVYI
GLEGGKEGGMARIGSIYVVPLLVFNAWITMVTYLQHHDEDTKVYAEGEWNYIKGALETIDREYGMGIDDLSHNITDGHVAHHLFFTQIPHYHLTAATAAVRQC
LQPTGTYKKRRSWNFLARFTELNYRLKYVAGQGVLSYVDWEVARKTPASAVTSSFSSSSSSSLPAEAAVKAAAAVPVAAVAAPVREGRPTRKRSPTRSSSPP

FIG. 9

MHVYPDKHEVIVSMEPMVEGMLSKLLLPTGEKAWQPSDFVPDLTKEGWEDEVKEFREKAETLPDETLVVLVGDMVTEEALPTYQTLLNTFEGVDDP
TGTSPSAWCRWTRGWTSEENRHGDLLNRYLYLTGRVDMRAIECTIQHLISSGFNPKIKKDPYKGFVYTSFQERATKISHQNVARLANSAGDGNLGLICS
KIAGDESRHEKAYQAIFQEILKKDPEGGLKSFYELMSDQITMPAVMMTDGHDPDLFEHFSVTAQKLGVYTAVDYANILEYLVETWDIEHMGGLSSEGA
KYQEKLCKLAPRYMRLAEMSLDRVKKMPKTPYSWIHGRVA

FIG. 10

MVFQLARDSVSALVYHFKEGNLNWPMIIYLVLVHLAGYIGLTTILACKWQTLLEAFILWPITGLGITAGVHRLWAHRSYNATLPYRILLMLFNSIANQGSIY
HWSRDHRVHHKYSETDADPHNATRGFFFAHMGWLIVKKHPKVVEGGKQLDFSDLAADPVVRFQRDWDPWFAQFMCFVMPALVASRFWGEAFWN
AFWVAGALRYMLVLHFTWMVNSAAHLYGDHPYDPTMWPAENPLVSVVAIGEGWHNWHHRYPYDYAASEFGISQQFNPTKAFIDFFAAIGMVTNRK
RATGAWAKLKESRARDAANGKSMKDFKGRGSGSDYGTTNTNYAVSNKTVVTDKGAQQPGWEESNHPKYN

FIG. 11

ALGAL DESATURASES

CROSS-REFERENCE TO RELATED APPLICATIONS

The present application is a continuation of U.S. patent application Ser. No. 13/458,914 filed on Apr. 27, 2012, titled "Algal Desaturases now U.S. Pat. No. 8,440,805," which claims the benefit and priority of U.S. Provisional Patent Application Ser. No. 61/480,353 filed on Apr. 28, 2011, titled "Desaturases," both of which are hereby incorporated by reference.

The present application is related to U.S. Non-Provisional patent application Ser. No. 12/581,812 filed on Oct. 19, 2009, titled "Homologous Recombination in an Algal Nuclear Genome," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to algal desaturases.

SUMMARY OF THE INVENTION

Isolated nucleotide sequences encoding polypeptides having desaturase activity, which utilize fatty acids as substrates.

BRIEF DESCRIPTION OF THE DRAWINGS

FIG. 1 is a table of exemplary desaturases.

FIG. 2 illustrates the nucleotide sequence encoding desaturase 3 (SEQ ID NO:1).

FIG. 3 illustrates the nucleotide sequence encoding desaturase 5 (SEQ ID NO:2).

FIG. 4 illustrates the nucleotide sequence encoding desaturase 7 (SEQ ID NO:3).

FIG. 5 illustrates the nucleotide sequence encoding desaturase 9 (SEQ ID NO:4).

FIG. 6 illustrates the nucleotide sequence encoding desaturase 10 (SEQ ID NO:5).

FIG. 7 illustrates the amino acid sequence encoded by desaturase 3 (SEQ ID NO:6).

FIG. 8 illustrates the amino acid sequence encoded by desaturase 5 (SEQ ID NO:7).

FIG. 9 illustrates the amino acid sequence encoded by desaturase 7 (SEQ ID NO:8).

FIG. 10 illustrates the amino acid sequence encoded by desaturase 9 (SEQ ID NO:9).

FIG. 11 illustrates the amino acid sequence encoded by desaturase 10 (SEQ ID NO:10).

DETAILED DESCRIPTION OF THE INVENTION

A fatty acid is a carboxylic acid with a long aliphatic tail (chain), which is either saturated or unsaturated. Saturated fatty acids are long-chain carboxylic acids that usually have between 12 and 24 carbon atoms and have no double bonds. Unsaturated fatty acids have one or more double bonds between carbon atoms. Most naturally occurring fatty acids have a chain of an even number of carbon atoms, from 4 to 28. A fatty acid desaturase is an enzyme that removes two hydrogen atoms from a fatty acid, creating a carbon/carbon double bond. These desaturases are classified as either Delta desaturases, indicating that the double bond is created at a fixed position from the carboxyl group of a fatty acid (for example, a delta nine ("Δ9") desaturase creates a double bond at the 9th position from the carboxyl end) or classified as Omega desaturases (for example, an omega three ("ω3") desaturase, which creates the double bond between the third and fourth carbon from the methyl end of the fatty acid).

Provided herein are isolated nucleotide sequences encoding polypeptides having desaturase activity, which utilize fatty acids as substrates.

The inventors sequenced the entire genome of algal genus Nannochloropsis and identified genes involved in fatty acid metabolism. They identified various desaturases, including exemplary desaturases which they designated as desaturase 3 ("desat3"), desaturase 5 ("desat5"), desaturase 7 ("desat7"), desaturase 9 ("desat9"), and desaturase 10 ("desat10").

The inventors manipulated the activities of the above-specified exemplary desaturase genes by:

1. Overexpression of the subject desaturase gene with a strong promoter.

2. Promoter replacement or promoter insertion in front of the subject desaturase gene within the genome via homologous recombination.

3. Knock out of the subject desaturase gene via insertion of a transformation construct into the gene or replacement of a part of or the entire subject desaturase gene via homologous recombination.

Exemplary support for the above-mentioned methods may be found in U.S. Non-Provisional patent application Ser. No. 12/581,812 filed on Oct. 19, 2009, titled "Homologous Recombination in an Algal Nuclear Genome," U.S. Non-Provisional patent application Ser. No. 12/480,635 filed on Jun. 8, 2009, titled "VCP-Based Vectors for Algal Cell Transformation," and U.S. Non-Provisional patent application Ser. No. 12/480,611 filed on Jun. 8, 2009, titled "Transformation of Algal Cells," all of which are hereby incorporated by reference.

Accordingly, the inventors were able to manipulate the activities of the various exemplary desaturases for the purpose of modifying the contents of certain fatty acids within algal genus Nannochloropsis.

FIG. 1 is a table of exemplary desaturases. The table includes the number of the respective desaturase, captioned "Desaturase No.", the corresponding sequence identifier number, captioned "SEQ ID NO", the type of desaturase, captioned "Desaturase Type", the relative increase or decrease in desaturase gene regulation with respect to the presence or absence of Nitrogen, captioned "Times Up/Down Regulated in the Presence/Absence of Nitrogen", a first desaturase substrate, captioned "Substrate 1", the resulting first product, captioned "Product 1", a second desaturase substrate (if applicable), captioned "Substrate 2", the resulting second product (if applicable), captioned "Product 2", whether the desaturase gene was up-regulated or down-regulated in a particular mutant construct (with respect to the Substrate 1 to Product 1 reaction), captioned "Gene Regulation in Mutant Up/Down", the observed increase or decrease of the corresponding substrate to product reaction by a mutant construct (as compared to a wild-type Nannochloropsis control cell), captioned "Substrate 1 to Product 1 Conversion" whether the desaturase gene was up-regulated or down-regulated in a particular mutant construct (with respect to the Substrate 2 to Product 2 reaction)(if applicable), captioned "Gene Regulation in Mutant Up/Down" and the observed increase or decrease of the corresponding substrate to product reaction by a mutant construct (as compared to a wild-type Nannochloropsis control cell), captioned "Substrate 2 to Product 2 Conversion" (if applicable).

As shown in FIG. 1, the inventors identified five exemplary desaturases, designated as desaturase 3 ("desat3"), desaturase 5 ("desat5"), desaturase 7 ("desat7"), desaturase 9 ("desat9"), and desaturase 10 ("desat10"). Each desaturase has a corresponding SEQ ID NO, reflecting a nucleotide sequence for the respective desaturase. The desaturase type (which indicates corresponding enzymatic activity) is also shown in FIG. 1. The column captioned "Times Up/Down Regulated in the Presence/Absence of Nitrogen" reflects whole transcriptome comparisons of samples grown under Nitrogen sufficient ("N+") or Nitrogen deficient conditions ("N-"). The columns captioned "Substrate 1 to Product 1 Conversion" and "Substrate 2 to Product 2 Conversion" (if applicable) show the observed increase or decrease of the corresponding substrate to product reactions by a mutant construct (as compared to a wild-type Nannochloropsis control cell).

Referring again to the table in FIG. 1, desaturase 3, a Delta 12 desaturase, is approximately 1.5 times up-regulated in the absence of Nitrogen. Desaturase 3 increases the conversion of Palmitolenic acid (16:2(n-7)) to 6,9,12-hexadecatrienoic acid (16:3(n-4)) by approximately 85% (when compared to a wild-type Nannochloropsis control cell). Desaturase 3 also increases the conversion of Oleic acid, cis-9-octadecenoic acid (18:1(n-9)) to Linoleic acid, all-cis-9, 12-octadecadienoic acid (18:2(n-6)) by approximately 50% (when compared to a wild-type Nannochloropsis control cell).

Desaturase 5, as shown in the table in FIG. 1, is also a Delta 12 desaturase. Desaturase 5 is not regulated in the presence or absence of Nitrogen. Desaturase 5 decreases the conversion of Oleic acid, cis-9-octadecenoic acid (18:1(n-9)) to 12-octadecadienoic acid (18:2(n-6)) by approximately 100% (when compared to a wild-type Nannochloropsis control cell).

Desaturase 7, shown in the table in FIG. 1, is an Omega 3 desaturase. Desaturase 7 is approximately 4.0 times up-regulated in the presence of Nitrogen. Desaturase 7 decreases the conversion of Arachidonic acid, all-cis-5,8,11,14-eicosatetraenoic acid (20:4(n-6))("ARA") to Eicosapentaenoic acid, all-cis-5,8,11,14,17-eicosapentaenoic acid (20:5(n-3)) ("EPA") by approximately 60% (when compared to a wild-type Nannochloropsis control cell). In fact, the EPA to ARA ratio changes from about 7.5 to about 22, an approximate 200% increase. Desaturase 7 increases the conversion of Linoleic acid, all-cis-9, 12-octadecadienoic acid (18:2(n-6)) to α-Linolenic acid, all-cis-9,12,15-octadecatrienoic acid (18:3(n-3)) by approximately 650% (when compared to a wild-type Nannochloropsis control cell). In fact, the ratio of α-Linolenic acid, all-cis-9,12,15-octadecatrienoic acid (18:3 (n-3)) to Linoleic acid, all-cis-9, 12-octadecadienoic acid (18:2(n-6)) changes from approximately 2.5 to approximately 15.8, an approximate 550% increase.

Desaturase 9, shown in the table in FIG. 1, is a Delta 9 desaturase. Desaturase 9 is approximately 6.6 times up-regulated in the absence of Nitrogen. Desaturase 9 increases the conversion of Palmitic acid, or hexadecanoic acid (16:0) to Palmitoleic acid, cis-9-hexadecenoic acid (16:1(n-7)) by approximately 25%, while increasing the ratio of Palmitoleic acid, cis-9-hexadecenoic acid (16:1(n-7)) to Palmitic acid, or hexadecanoic acid (16:0) from about 0.48 to 0.6, an approximate increase of 25%.

Desaturase 10, shown in the table in FIG. 1, is a Delta 9 desaturase. Desaturase 9 is approximately 5.0 times up-regulated in the absence of Nitrogen. Desaturase 9 increases the conversion of Palmitic acid, or hexadecanoic acid (16:0) to Palmitoleic acid, cis-9-hexadecenoic acid (16:1(n-7)) by approximately 34%, while increasing the ratio of Palmitoleic acid, cis-9-hexadecenoic acid (16:1(n-7)) to Palmitic acid, or hexadecanoic acid (16:0) from about 1.02 to 1.19, an approximate increase of 16%.

FIG. 2 illustrates the nucleotide sequence encoding desaturase 3 (SEQ ID NO:1).

The inventors found that desaturase 3 is slightly up-regulated under Nitrogen starvation. The inventors prepared a construct utilizing desaturase 3 that included a strong upstream promoter. This resulted in expression of elevated amounts of 16:3n4 and 18:2n6 fatty acids.

FIG. 3 illustrates the nucleotide sequence encoding desaturase 5 (SEQ ID NO:2).

The inventors found that desaturase 5 encodes a fatty acid desaturase with high homology to Delta 12 desaturases. The inventors also found that overexpression of this desaturase gene under the control of an inducible Urease promoter leads to higher expression levels of 18:1n9 fatty acids and poly unsaturated fatty acids ("PUFAs") with 18 or more carbon atoms, when the constructs are grown under Nitrogen starvation conditions (please note: the promoter is induced under Nitrogen starvation).

In other experiments, the inventors determined that the desaturation step at the Delta 12 position is likely a major bottleneck for channeling carbon into the PUFA biosynthesis pathway. While 18:1n9 fatty acids are steadily increasing during Nitrogen starvation, 18:2n6 fatty acids (derived from the Delta 12 desaturation of said 18:1n9 fatty acids) are decreasing, as are all fatty acids in the pathway leading to the production of Eicosapentaenoic acid ("EPA"). The inventors concluded that the desaturase 5 gene increases carbon flux into the PUFA biosynthesis pathway during Nitrogen starvation if the desaturase 5 gene is over-expressed.

FIG. 4 illustrates the nucleotide sequence encoding desaturase 7 (SEQ ID NO:3).

The inventors prepared various constructs (promoter replacements, knock-outs, and over expression constructs) and found that down-regulation of the desaturase 7 gene results in a lower EPA/Arachidonic acid ("ARA") ratio, i.e. less ARA is desaturated to EPA. The inventors observed in mutant constructs that lower desaturase 7 transcription is due to an exchange of the native promoter in the wild-type Nannochloropsis cells. The inventors observed that the mutant constructs had nearly double the levels of ARA with less levels of EPA, when compared to the wild-type Nannochloropsis control cells.

The inventors also observed that up-regulation of the desaturase 7 gene results in higher 18:3n3/18:2n6 and EPA/ARA ratios, i.e. more 18:2n6 is converted to 18:3n3, and more ARA is converted into EPA. Accordingly, the inventors observed that the EPA/ARA ratio was nearly doubled.

FIG. 5 illustrates the nucleotide sequence encoding desaturase 9 (SEQ ID NO:4).

FIG. 6 illustrates the nucleotide sequence encoding desaturase 10 (SEQ ID NO:5).

The inventors observed that both desaturase 9 and desaturase 10 appear to be Delta 9 desaturases acting primarily on 16:0 fatty acids or on 16:0 fatty acids attached to other compounds. Promotor exchange studies, in which the inventors exchanged the native wild-type promoter of Nannochloropsis against a strong promoter, revealed an up-regulation of said activity under Nitrogen deficient conditions. Thus, under Nitrogen starvation, a high percentage of fatty acids are channeled to the accumulation of 16:1n7 fatty acids through the action of the desaturase 9 gene, meaning less fatty acids are entering the PUFA pathway. The inventors also replaced the promoters of the desaturase 9 genes with promoters of moderate strength and which are putatively not regulated when cells enter Nitrogen starvation, with the goal to avoid carbon flux into the biosynthesis of 16:1n7 and 18:1n7 fatty acids and to increase carbon flux into the PUFA biosynthesis pathway during starvation. The inventors found that these genes are excellent targets for over-expression, in order to achieve elevated PUFA biosynthesis. Down-regulation of these (or other) genes, as an example, by replacement of the endogenous promoter or insertion of a weaker promoter in front of the respective desaturase gene may lead to a higher content of short chain fatty acids. Down-regulation of transcription could also be achieved, in some cases, by insertion of a commonly strong promoter in front of the respective desaturase gene, presumably by modifying the respective chromatin arrangement around the desaturase gene, thus leading to a lower transcription level. Also, the introduction of point mutations into the desaturase gene when inserting another promoter in front of the desaturase gene via the homologous recombination flanks may lead to an altered activity of the respective gene products.

The inventors also observed an increase of 16:1n7 lipids in a selected desaturase 10 over expression mutant, clearly demonstrating that there is an approximately 40% increase in 16:1n7 fatty acids in this mutant when compared to the wild-type Nannochloropsis cells during the same experiment.

FIG. 7 illustrates the amino acid sequence encoded by desaturase 3 (SEQ ID NO:6).

FIG. 8 illustrates the amino acid sequence encoded by desaturase 5 (SEQ ID NO:7).

FIG. 9 illustrates the amino acid sequence encoded by desaturase 7 (SEQ ID NO:8).

FIG. 10 illustrates the amino acid sequence encoded by desaturase 9 (SEQ ID NO:9).

FIG. 11 illustrates the amino acid sequence encoded by desaturase 10 (SEQ ID NO:10).

While various embodiments have been described above, it should be understood that they have been presented by way of example only, and not limitation. Thus, the breadth and scope of a preferred embodiment should not be limited by any of the above-described exemplary embodiments.

What is claimed is:

1. A transformation vector comprising an isolated nucleotide sequence encoding a polypeptide having desaturase activity, the nucleotide sequence set forth as SEQ ID NO:1.

2. The transformation vector of claim 1 wherein the transformation vector encodes a functionally active desaturase which utilizes a fatty acid as a substrate.

3. The transformation vector of claim 2, wherein the functionally active desaturase comprises amino acids having the sequence set forth as SEQ ID NO:6.

4. A transformation vector comprising an isolated nucleotide sequence encoding a polypeptide having desaturase activity, the nucleotide sequence having at least 95% sequence identity to SEQ ID NO:2.

5. The transformation vector sequence of claim 4 wherein the transformation vector encodes a functionally active desaturase which utilizes a fatty acid as a substrate.

6. The transformation vector of claim 5, wherein the functionally active desaturase comprises amino acids having the sequence set forth as SEQ ID NO:7.

7. The transformation vector of claim 1 wherein the transformation vector is derived from algae.

8. The transformation vector of claim 7 wherein the algae is of genus *Nannochloropsis*.

* * * * *

SEQUENCE LISTING

```
<160> NUMBER OF SEQ ID NOS: 10

<210> SEQ ID NO 1
<211> LENGTH: 1698
<212> TYPE: DNA
<213> ORGANISM: Nannochloropsis

<400> SEQUENCE: 1

atgggacgcg gtggcgagcg ggtcgagacg acggagtctt tgagcttcac ggccgacaag     60

gcggggacca tcaagcagcg tggggggaag atcacatggg atgaggtatg tgacggggca    120

tggaggcgtc ggacggagga atgcagggag aaagggaaag agaggagaaa ggaaagcaag    180

gtgtatctgc tgtggcggta gatttgccat ctatatgatc ctttgagtgc agtgcttgga    240

tggaaggcgt cagtgcaatc ctgtatgtga tgacggagga agcagcacac cttcccttcc    300

ctaatctctg tcccctacaa ccccgcgtat cctcttctcc cgatcaccca cgctcacaca    360

cacctattta ctctccaggt gcgtcagcac aagacgcctc aggacgcttg gctcgtgtat    420

aggaataagg tctacgacgt gtcgggctgg caagatcacc ccggggggaa cgtcatcttc    480

actcacgccg gcggggactg cacggatatt ttcgcggcgt tccaccctct tggcgccacc    540

tcttatcttg atccatttta cattggcgag ctggagccgg gctcggacaa gaagcccgca    600

gcgcaggcga actttgagcg ggcctacagg gatctcaggg ggaagcttat cgcgggtggg    660

tttttcaagg cgaatccttt gtactatgtc tggaaggtag tatcgacagt tgcccttgct    720

gtaggtgcgt ggatgctggt ggcttggtcg cagaacctgg gcgtgcagat gctgtctgcg    780

tttttggtgg ctctgttctg gcagcaatgt ggctggttgg cccatgactt cctgcaccac    840

caggtattta agaaccgtgc gttgggtgac ctggccggca tcgttatcgg caatgtcttc    900

cagggtttct ccgtggcatg gtggaagaac aagcataaca ctcaccacgc ggtgcccaac    960

ctcgtcgagt cctctccgga cgcgcaagac ggagaccctg acattgacac catgcccata   1020

ctggcctggt cgctcaagat ggccgacagg gcgcagcaat actcatgggg acccttcttt   1080

gtcaggcatc agtcgctgct atacttcccc atcctgctcg tggcgcggat ttcatggttg   1140
```

-continued atgcagtcgt tcttgtttgt ctttgactcc gtccctggag cgagtctgtg ggcaaccaag 1200
ggcgcgacgg ctgagagaca ggcgatcaag aatgtcgggt tggagaaggt ggggctggtt 1260
gcgcactacc tgtggtacgg tgcgctgatg ctgtgccaca tgtccctggc ccgcgccctg 1320
ctgtacttcc tggcgagcca gatgatgtgc gggttcttgc tcgcgcttgt tttcgggctt 1380
gggcacaacg gcatggctgt ttacgacgcg gacgcccggc ccgacttctg gaagctgcag 1440
gtgacgacga cgaggaacgt gacgggctcg tggttggtgc agtggttctg tggcggcctc 1500
ggctaccagg tggaccacca cctgttcccc atgatcccgc ggcaccgcct agggaagctc 1560
cacgggctcg tggagggttt ctgcaaggat cacggggtga agtaccacga gacgaatatg 1620
tgggagggga ccaaagaggt gttggctcac ttgagcagtg tgacgaaaga gttcgtggcc 1680
gatttccccg ccatgtaa 1698

<210> SEQ ID NO 2
<211> LENGTH: 1576
<212> TYPE: DNA
<213> ORGANISM: Nannochloropsis

<400> SEQUENCE: 2
atgggacgcg gcggtgagaa gacggtgacc cctcttcgca aaaaaaccct cctggatgcc 60
gcttccacga tcagcggcac agtcagacca agcaaggcag tagaggccct gcccacggag 120
gagctgcgta agaaggccgc acaatacggt atcaacactt cggtcgaccg cgaaacactg 180
ctgagggagc tggtaagtgc ttgtgatcgc ttgaggggtg gatgggtaaa aacagttccc 240
tcccattcgt gcatgtggtc agacggatat aagaattacg tgccatgccc ttgacatttt 300
gatgtcaccg cgctgtcttc acttcccgct ccaatagcta ttatgtacgt ggactggcgg 360
ctgctgcccc ttgtcctttt ttcttccctc ccttgcatgc cacctaagca tacctcgctc 420
attcactttc cgcatgtcat cataaccaca ggctccctac ggcgatatcc tcctccgcaa 480
tgacgcccct aaatccctgc cccttgcccc tcctcctttc accctctccg acatcaagaa 540
cgctgttccc cgtcactgct ttgagcgttc cctctccacc tccctcttcc acttgaccat 600
cgacttgatc caagtcgctg tcctcgggta ccttgcctca ttactgggcc actccgacgt 660
cccgcccatg tctcgttata ttctatggcc gttgtactgg tacgcgcaag gctctgtgct 720
gacgggagtg tgggtcattg cccacgagtg cgggcaccaa tcgttttcgc cttacgagag 780
cgtgaacaac ttctttgggt ggctcttgca ctcggccttg cttgtgccct atcactcttg 840
gaggatttcc catggaaagc accacaacaa cacggggagc tgcgagaatg acgaggtctt 900
tgcgccgcct attaaggagg aactgatgga cgagattttg cttcactccc ctttggcgaa 960
tctggtgcag ataatcataa tgttgaccat cggatggatg ccggggtacc tgctcctgaa 1020
cgctacgggg cctaggaaat acaagggact gagcaatagc cactttaacc caaattcggc 1080
gttgttttct ccgaaggacc gtctggacat tatttggtcc gacattgggt ttttcgtggc 1140
cttggcctgc gtggtatatg cctgtgtgca gtttggattt caaacggtgg gaaagtatta 1200
cctgctgccg tacatggtgg tcaattatca cctggtcctc atcacgtacc tgcagcacac 1260
ggacgtcttc atcccccact ttcgggggag cgagtggacg tggtttaggg gcgccctttg 1320
cacggtcgac cgatccttcg gctggctttt ggaccatacg tttcaccata tcagtgacac 1380
tcatgtgtgc caccacatct tcagcaagat gccgttctac cacgcgcagg aggcgagtga 1440
gcacattcgc aaggcgttgg gcgactatta tttgaaggat gataccccga tttggaaggc 1500
attgtggcga agttataccc tgtgcaagta cgtggactcg gaggagacga cggtattcta 1560

-continued

```
caagcagcgg gcatag                                                 1576

<210> SEQ ID NO 3
<211> LENGTH: 2317
<212> TYPE: DNA
<213> ORGANISM: Nannochloropsis

<400> SEQUENCE: 3

atggttgagc aaacgttacc gaccttgtcc cagatcaaga aagccatccc cgagaaatgc     60

ttccaggtac aacgcggagg gggtggaggg ggggggagtg aagcaggggg gggggagaac    120

gggtgataaa gagggatagg ttgagagaat ggaagaggga aaagggaaga agtgttgcaa    180

ggacgtggtg ttgcaaggac gtggtgtacc tgtgcgtacc cgacccgcgt gtccacaagc    240

tcgagcagtc cgaagcgctt tgtcaccctt ctcaccacat atccctccct cctgtctcca    300

tttcctccct tcagaaatcc ctcctccgct ccttttacta catgctgagg gacttcgcgg    360

ccttggcggc actctacttt gtttatccca cagtgcaggc caagtatgga ttgcctggtt    420

tgtttgtgtg gtggaacctc gcaggtaggg agggagggag gatgagaggg aagagaattg    480

gggaaagcca tcgagccgtc ttatacgtct tctaggcact cacaaactct tctcccctcc    540

ctcctcccct tcctccccag gctttttcat gtggtgcctc ttcgtgatag gccacgattg    600

cggccatggc tccttctccg agtacaagtg gctcaatgac atatgcggtc acatttgcca    660

cgccccccttg atggtgcctt actggccttg gcagaaggta tgggagccag gccgccctcc    720

ctccttccct ccctcccccc ttccctcgtt ttaatgacat gtcgatcatc tcattcattc    780

tatctctgcc tcccttcctc cctacctccc tccctccatc cctttcgcca gtcccaccgc    840

cttcaccaca tgtaccacaa ccacctgact aaggacatgt cacacccgtg gatgaccaag    900

gaggtgttcg aggtaggaag ggagggaggg cggatatgtt gttgggatga acgctataga    960

gaaggcacgg gcttgtttga tcctgtggca tacctcacgc cttccctccc tccctccctc   1020

cctccctccc tttttttca ggacttgacc ccattcgagc aggcgttgct ggagaacccg   1080

ctgtccctct tcatcaagta caccttcctt tacctctttg cgggcaagat ggatggcagg   1140

tatgaagagg gatgagggca gaggacggat gagggagagg acgggaagtc ggacacggag   1200

tgggctcgct tcttgtccca ctctcgattg ctcaccctcc ctccctccct ccctccctcc   1260

ctccctccct cccttccgtc tggacacagc catgtagttc cattctcccc cctcttcacc   1320

gacaccaagg agcgggtgca atgcgctgtg tcgacgctgg gtatggtcgt cgcaggcgcc   1380

cttgtgtaca tcgggctcga gggcgggaag gagggaggga tggcgaggat aggatccatt   1440

tatgtggtgc cgttgctggt gttcaatgcc tggatcacga tggtgacata cctgcagcac   1500

cacgatgagg acaccaaggt ttatgcagag gggagtgga actacatcaa gggggccctg   1560

gagacgatcg accgcgaata cggcatgggg attgacggtg agtttatcat tggttaaata   1620

tattgtgaca actctaatta attgattact ttcatgtttt aattgacaat tcgttctcgg   1680

tgatggtgag gacaccaagg tgacagtttc ccacagctct gtcttagcct caagactaag   1740

ctggcctcct ttcctcccgc cctcccttcc cttagacctc tcccacaata tcacggatgg   1800

ccacgtggcg caccacctct tcttcacgca gatcccgcac taccacctga cggcggccac   1860

ggccgctgtg agacaatgcc tgcaacctac ggggacctac aagaagagga ggagctggaa   1920

ttttctcgct cgtttcacgg agcttaacta ccgtttgaaa tacgtcgcgg gccagggcgt   1980

gctctcctat gtggattggg aggtaaggga aggaggaaga gcgaaggagt gagggaaaga   2040
```

-continued

```
gtgaggaaaa gtaaatatag atggagggtt tgcgagctca gctttcttcc ttctcaccct   2100

tgctccctcc ctcgtcttgt aaccatcaca ggtcgctcgc aagacccctg cttccgccgt   2160

cacctcctct ttctcttcct cctcctcttc ctcccttccg gcagaggctg ctgtcaaggc   2220

ggctgctgcc gttcccgttg ctgctgttgc tgctcccgtc cgagaaggaa gaccaacacg   2280

caagcgctct cccacccgtt catcctcccc tccgtaa                            2317
```

<210> SEQ ID NO 4
<211> LENGTH: 1305
<212> TYPE: DNA
<213> ORGANISM: Nannochloropsis

<400> SEQUENCE: 4

```
atgcacgtct accccgacaa gcacgaagtc attgtcagca tggagcccat ggtggaaggg     60

atgctctcga agctcctcct ccccacgggg gagaaggctt ggcaaccgtc cgactttgtc    120

ccggacctga ccaaggaagg gtgggaagac gaggtaaagg aattcaggga aaaggcggag    180

acgttgccgg acgagacgct ggtggtcttg gtgggggaca tggtgactga ggaggcgttg    240

cccacttacc agacgctgtt gaacacgttc gagggcgtgg atgaccccac cgggacgagt    300

ccttcggcct ggtgccgatg gacacggggg tggacgagcg aggagaacag gcacggggat    360

ctgctcaacc ggtacttgta cttgacgggg cgcgtggaca tgcgcgcgat cgagtgcacg    420

attcagcacc tggtacgtgg ggatgggagg gagggagaga gggagggatg gaggaaggct    480

cctgttcttg tgttcccccc cttcgtctcg cgcgatgtct aactcattct tcccaccctc    540

cctccctctg cgtccgtaaa ttagatttcg agcggtttca accccaaaat caagaaggat    600

ccgtacaagg gtttcgtata cacctccttc caagagcgag caaccaagat ctcccatcag    660

aatgtggcgc ggctggccaa cagcgccggt gatggcaatc tgggtctgat ctgcagtaag    720

attgcagggg atgagtcgag gcacgagaag gcataccaag ccatcttcca ggagatcctc    780

aagaaggacc cggaaggggg gttgaagagc ttctatgagt taatgagtga tcaggtaggg    840

agggcggagg agagggaggg ggaaagggag ggaggtaggt acgcattagg aggcaggagg    900

aagggaacga cacaagtact ttcaccatgg gccaagatac ggctgtttac ctttccctcc    960

tccctccctc tctccctccc tccctccctc cctccctcat ctcagatcac catgcctgcc   1020

gtgatgatga cggacggcca cgacccggac ctcttcgagc acttctcggt cacggcgcag   1080

aagctcggtg tctacacggc agtggactac gccaacattc tggaatattt ggtggagaca   1140

tgggacatcg agcacatggg aggcctgtct tctgaagggg ccaagtacca ggagaagctc   1200

tgcaagctcg cgccccgata catgaggctt gccgagatga gtcttgaccg ggtgaaaaag   1260

atgcccaaga cgccttattc ttggatccat ggacgcgtgg cttaa                   1305
```

<210> SEQ ID NO 5
<211> LENGTH: 1080
<212> TYPE: DNA
<213> ORGANISM: Nannochloropsis

<400> SEQUENCE: 5

```
atggtcttcc agctcgcccg agactctgtc tcggccctgg tctatcattt caaagaagga     60

aaccttaact ggcctatgat tatctacctc gtccttgtcc acttggcggg ctacatcggt    120

ctgactacca ttctggcttg caaatggcaa actctcctcg aagcgttcat cctatggccc    180

atcaccgggc tggggattac tgccggcgta caccgacttt gggcacaccg ttcgtacaat    240

gccacgttgc cttatcgcat cctgttgatg ttgttcaact caattgcgaa ccaaggcagc    300
```

atctaccact ggtcccggga ccaccgcgtg caccacaagt actccgagac tgatgctgac 360
ccacataacg ccacccgtgg cttcttcttc gcgcacatgg gctggctcat tgttaagaag 420
caccccaagg tcgtcgaagg ggggaagcaa ctcgatttct ccgatttggc tgccgatccc 480
gtggtgcgat tccagcgtga ttgggatccg tggttcgccc agtttatgtg ctttgtcatg 540
ccggcgcttg ttgcatcgag gttctggggt gaggcgttct ggaacgcctt ttgggtggcg 600
ggggctttga ggtatatgtt ggtgctgcac ttcacctgga tggttaacag tgcggcgcac 660
ttgtatggcg accacccgta cgaccctacc atgtggccgg cggagaaccc gttggtatcg 720
gtagtggcga tcggagaagg ctggcataac tggcaccatc gttacccccta cgactacgcg 780 gcttccgagt ttgggatttc gcagcagttc aacccgacca aggcgttcat tgattttttt 840
gcggccatag ggatggtgac gaaccgaaaa cgtgcgacgg gggcttgggc aaagctcaag 900
gaatccaggg caagggatgc ggcgaatggg aagagcatga aagatttcaa gggaagaggc 960
tcggggtcag actatggtac gacaaacacc aattacgcgg tgtcgaacaa gacagtggtg 1020
accgacaagg gggcgcaaca accagggtgg gaggagagca atcaccccaa gtacaactaa 1080

<210> SEQ ID NO 6
<211> LENGTH: 440
<212> TYPE: PRT
<213> ORGANISM: Nannochloropsis

<400> SEQUENCE: 6

```
Met Val Arg Gln His Lys Thr Pro Gln Asp Ala Trp Leu Val Tyr Arg
1               5                   10                  15

Asn Lys Val Tyr Asp Val Ser Gly Trp Gln Asp His Pro Gly Gly Asn
            20                  25                  30

Val Ile Phe Thr His Ala Gly Gly Asp Cys Thr Asp Ile Phe Ala Ala
        35                  40                  45

Phe His Pro Leu Gly Ala Thr Ser Tyr Leu Asp Pro Phe Tyr Ile Gly
    50                  55                  60

Glu Leu Glu Pro Gly Ser Asp Lys Lys Pro Ala Ala Gln Ala Asn Phe
65                  70                  75                  80

Glu Arg Ala Tyr Arg Asp Leu Arg Gly Lys Leu Ile Ala Gly Gly Phe
                85                  90                  95

Phe Lys Ala Asn Pro Leu Tyr Tyr Val Trp Lys Val Val Ser Thr Val
            100                 105                 110

Ala Leu Ala Val Gly Ala Trp Met Leu Val Ala Trp Ser Gln Asn Leu
        115                 120                 125

Gly Val Gln Met Leu Ser Ala Phe Leu Val Ala Leu Phe Trp Gln Gln
    130                 135                 140

Cys Gly Trp Leu Ala His Asp Phe Leu His His Gln Val Phe Lys Asn
145                 150                 155                 160

Arg Ala Leu Gly Asp Leu Ala Gly Ile Val Ile Gly Asn Val Phe Gln
                165                 170                 175

Gly Phe Ser Val Ala Trp Trp Lys Asn Lys His Asn Thr His His Ala
            180                 185                 190

Val Pro Asn Leu Val Glu Ser Ser Pro Asp Ala Gln Asp Gly Asp Pro
        195                 200                 205

Asp Ile Asp Thr Met Pro Ile Leu Ala Trp Ser Leu Lys Met Ala Asp
    210                 215                 220

Arg Ala Gln Gln Tyr Ser Trp Gly Pro Phe Phe Val Arg His Gln Ser
225                 230                 235                 240
```

```
Leu Leu Tyr Phe Pro Ile Leu Leu Val Ala Arg Ile Ser Trp Leu Met
                245                 250                 255

Gln Ser Phe Leu Phe Val Phe Asp Ser Val Pro Gly Ala Ser Leu Trp
            260                 265                 270

Ala Thr Lys Gly Ala Thr Ala Glu Arg Gln Ala Ile Lys Asn Val Gly
        275                 280                 285

Leu Glu Lys Val Gly Leu Val Ala His Tyr Leu Trp Tyr Gly Ala Leu
    290                 295                 300

Met Leu Cys His Met Ser Leu Ala Arg Ala Leu Leu Tyr Phe Leu Ala
305                 310                 315                 320

Ser Gln Met Met Cys Gly Phe Leu Leu Ala Leu Val Phe Gly Leu Gly
                325                 330                 335

His Asn Gly Met Ala Val Tyr Asp Ala Asp Ala Arg Pro Asp Phe Trp
            340                 345                 350

Lys Leu Gln Val Thr Thr Thr Arg Asn Val Thr Gly Ser Trp Leu Val
        355                 360                 365

Gln Trp Phe Cys Gly Gly Leu Gly Tyr Gln Val Asp His His Leu Phe
    370                 375                 380

Pro Met Ile Pro Arg His Arg Leu Gly Lys Leu His Gly Leu Val Glu
385                 390                 395                 400

Gly Phe Cys Lys Asp His Gly Val Lys Tyr His Glu Thr Asn Met Trp
                405                 410                 415

Glu Gly Thr Lys Glu Val Leu Ala His Leu Ser Ser Val Thr Lys Glu
            420                 425                 430

Phe Val Ala Asp Phe Pro Ala Met
        435                 440


<210> SEQ ID NO 7
<211> LENGTH: 438
<212> TYPE: PRT
<213> ORGANISM: Nannochloropsis

<400> SEQUENCE: 7

Met Gly Arg Gly Gly Glu Lys Thr Val Thr Pro Leu Arg Lys Lys Thr
1               5                   10                  15

Leu Leu Asp Ala Ala Ser Thr Ile Ser Gly Thr Val Arg Pro Ser Lys
            20                  25                  30

Ala Val Glu Ala Leu Pro Thr Glu Glu Leu Arg Lys Lys Ala Ala Gln
        35                  40                  45

Tyr Gly Ile Asn Thr Ser Val Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Pro Phe Thr Leu Ser Asp Ile Lys Asn Ala Val
                85                  90                  95

Pro Arg His Cys Phe Glu Arg Ser Leu Ser Thr Ser Leu Phe His Leu
            100                 105                 110

Thr Ile Asp Leu Ile Gln Val Ala Val Leu Gly Tyr Leu Ala Ser Leu
        115                 120                 125

Leu Gly His Ser Asp Val Pro Pro Met Ser Arg Tyr Ile Leu Trp Pro
    130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
```

-continued

```
                165                 170                 175

Asn Phe Phe Gly Trp Leu Leu His Ser Ala Leu Leu Val Pro Tyr His
            180                 185                 190

Ser Trp Arg Ile Ser His Gly Lys His His Asn Asn Thr Gly Ser Cys
        195                 200                 205

Glu Asn Asp Glu Val Phe Ala Pro Pro Ile Lys Glu Glu Leu Met Asp
    210                 215                 220

Glu Ile Leu Leu His Ser Pro Leu Ala Asn Leu Val Gln Ile Ile Ile
225                 230                 235                 240

Met Leu Thr Ile Gly Trp Met Pro Gly Tyr Leu Leu Leu Asn Ala Thr
                245                 250                 255

Gly Pro Arg Lys Tyr Lys Gly Leu Ser Asn Ser His Phe Asn Pro Asn
            260                 265                 270

Ser Ala Leu Phe Ser Pro Lys Asp Arg Leu Asp Ile Ile Trp Ser Asp
        275                 280                 285

Ile Gly Phe Phe Val Ala Leu Ala Cys Val Val Tyr Ala Cys Val Gln
    290                 295                 300

Phe Gly Phe Gln Thr Val Gly Lys Tyr Tyr Leu Leu Pro Tyr Met Val
305                 310                 315                 320

Val Asn Tyr His Leu Val Leu Ile Thr Tyr Leu Gln His Thr Asp Val
                325                 330                 335

Phe Ile Pro His Phe Arg Gly Ser Glu Trp Thr Trp Phe Arg Gly Ala
            340                 345                 350

Leu Cys Thr Val Asp Arg Ser Phe Gly Trp Leu Leu Asp His Thr Phe
        355                 360                 365

His His Ile Ser Asp Thr His Val Cys His His Ile Phe Ser Lys Met
    370                 375                 380

Pro Phe Tyr His Ala Gln Glu Ala Ser Glu His Ile Arg Lys Ala Leu
385                 390                 395                 400

Gly Asp Tyr Tyr Leu Lys Asp Asp Thr Pro Ile Trp Lys Ala Leu Trp
                405                 410                 415

Arg Ser Tyr Thr Leu Cys Lys Tyr Val Asp Ser Glu Glu Thr Thr Val
            420                 425                 430

Phe Tyr Lys Gln Arg Ala
        435


<210> SEQ ID NO 8
<211> LENGTH: 410
<212> TYPE: PRT
<213> ORGANISM: Nannochloropsis

<400> SEQUENCE: 8

Met Val Glu Gln Thr Leu Pro Thr Leu Ser Gln Ile Lys Lys Ala Ile
1               5                   10                  15

Pro Glu Lys Cys Phe Gln Lys Ser Leu Leu Arg Ser Phe Tyr Tyr Met
            20                  25                  30

Leu Arg Asp Phe Ala Ala Leu Ala Ala Leu Tyr Phe Val Tyr Pro Thr
        35                  40                  45

Val Gln Ala Lys Tyr Gly Leu Pro Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Leu Asn Asp Ile Cys Gly His
                85                  90                  95
```

-continued

Ile Cys His Ala Pro Leu Met Val Pro Tyr Trp Pro Trp Gln Lys Ser
100 105 110

His Arg Leu His His Met Tyr His Asn His Leu Thr Lys Asp Met Ser
115 120 125

His Pro Trp Met Thr Lys Glu Val Phe Glu Asp Leu Thr Pro Phe Glu
130 135 140

Gln Ala Leu Leu Glu Asn Pro Leu Ser Leu Phe Ile Lys Tyr Thr Phe
145 150 155 160

Leu Tyr Leu Phe Ala Gly Lys Met Asp Gly Ser His Val Val Pro Phe
165 170 175

Ser Pro Leu Phe Thr Asp Thr Lys Glu Arg Val Gln Cys Ala Val Ser
180 185 190

Thr Leu Gly Met Val Val Ala Gly Ala Leu Val Tyr Ile Gly Leu Glu
195 200 205

Gly Gly Lys Glu Gly Gly Met Ala Arg Ile Gly Ser Ile Tyr Val Val
210 215 220

Pro Leu Leu Val Phe Asn Ala Trp Ile Thr Met Val Thr Tyr Leu Gln
225 230 235 240

His His Asp Glu Asp Thr Lys Val Tyr Ala Glu Gly Glu Trp Asn Tyr
245 250 255

Ile Lys Gly Ala Leu Glu Thr Ile Asp Arg Glu Tyr Gly Met Gly Ile
260 265 270

Asp Asp Leu Ser His Asn Ile Thr Asp Gly His Val Ala His His Leu
275 280 285

Phe Phe Thr Gln Ile Pro His Tyr His Leu Thr Ala Ala Thr Ala Ala
290 295 300

Val Arg Gln Cys Leu Gln Pro Thr Gly Thr Tyr Lys Lys Arg Arg Ser
305 310 315 320

Trp Asn Phe Leu Ala Arg Phe Thr Glu Leu Asn Tyr Arg Leu Lys Tyr
325 330 335

Val Ala Gly Gln Gly Val Leu Ser Tyr Val Asp Trp Glu Val Ala Arg
340 345 350

Lys Thr Pro Ala Ser Ala Val Thr Ser Ser Phe Ser Ser Ser Ser Ser
355 360 365

Ser Ser Leu Pro Ala Glu Ala Ala Val Lys Ala Ala Ala Ala Val Pro
370 375 380

Val Ala Ala Val Ala Ala Pro Val Arg Glu Gly Arg Pro Thr Arg Lys
385 390 395 400

Arg Ser Pro Thr Arg Ser Ser Ser Pro Pro
405 410

<210> SEQ ID NO 9
<211> LENGTH: 333
<212> TYPE: PRT
<213> ORGANISM: Nannochloropsis

<400> SEQUENCE: 9

Met His Val Tyr Pro Asp Lys His Glu Val Ile Val Ser Met Glu Pro
1 5 10 15

Met Val Glu Gly Met Leu Ser Lys Leu Leu Leu Pro Thr Gly Glu Lys
20 25 30

Ala Trp Gln Pro Ser Asp Phe Val Pro Asp Leu Thr Lys Glu Gly Trp
35 40 45

Glu Asp Glu Val Lys Glu Phe Arg Glu Lys Ala Glu Thr Leu Pro Asp
50 55 60

-continued

Glu Thr Leu Val Val Leu Val Gly Asp Met Val Thr Glu Glu Ala Leu
65 70 75 80

Pro Thr Tyr Gln Thr Leu Leu Asn Thr Phe Glu Gly Val Asp Asp Pro
85 90 95

Thr Gly Thr Ser Pro Ser Ala Trp Cys Arg Trp Thr Arg Gly Trp Thr
100 105 110

Ser Glu Glu Asn Arg His Gly Asp Leu Leu Asn Arg Tyr Leu Tyr Leu
115 120 125

Thr Gly Arg Val Asp Met Arg Ala Ile Glu Cys Thr Ile Gln His Leu
130 135 140

Ile Ser Ser Gly Phe Asn Pro Lys Ile Lys Lys Asp Pro Tyr Lys Gly
145 150 155 160

Phe Val Tyr Thr Ser Phe Gln Glu Arg Ala Thr Lys Ile Ser His Gln
165 170 175

Asn Val Ala Arg Leu Ala Asn Ser Ala Gly Asp Gly Asn Leu Gly Leu
180 185 190

Ile Cys Ser Lys Ile Ala Gly Asp Glu Ser Arg His Glu Lys Ala Tyr
195 200 205

Gln Ala Ile Phe Gln Glu Ile Leu Lys Lys Asp Pro Glu Gly Gly Leu
210 215 220

Lys Ser Phe Tyr Glu Leu Met Ser Asp Gln Ile Thr Met Pro Ala Val
225 230 235 240

Met Met Thr Asp Gly His Asp Pro Asp Leu Phe Glu His Phe Ser Val
245 250 255

Thr Ala Gln Lys Leu Gly Val Tyr Thr Ala Val Asp Tyr Ala Asn Ile
260 265 270

Leu Glu Tyr Leu Val Glu Thr Trp Asp Ile Glu His Met Gly Gly Leu
275 280 285

Ser Ser Glu Gly Ala Lys Tyr Gln Glu Lys Leu Cys Lys Leu Ala Pro
290 295 300

Arg Tyr Met Arg Leu Ala Glu Met Ser Leu Asp Arg Val Lys Lys Met
305 310 315 320

Pro Lys Thr Pro Tyr Ser Trp Ile His Gly Arg Val Ala
325 330

<210> SEQ ID NO 10
<211> LENGTH: 359
<212> TYPE: PRT
<213> ORGANISM: Nannochloropsis

<400> SEQUENCE: 10

Met Val Phe Gln Leu Ala Arg Asp Ser Val Ser Ala Leu Val Tyr His
1 5 10 15

Phe Lys Glu Gly Asn Leu Asn Trp Pro Met Ile Ile Tyr Leu Val Leu
20 25 30

Val His Leu Ala Gly Tyr Ile Gly Leu Thr Thr Ile Leu Ala Cys Lys
35 40 45

Trp Gln Thr Leu Leu Glu Ala Phe Ile Leu Trp Pro Ile Thr Gly Leu
50 55 60

Gly Ile Thr Ala Gly Val His Arg Leu Trp Ala His Arg Ser Tyr Asn
65 70 75 80

Ala Thr Leu Pro Tyr Arg Ile Leu Leu Met Leu Phe Asn Ser Ile Ala
85 90 95

Asn Gln Gly Ser Ile Tyr His Trp Ser Arg Asp His Arg Val His His

-continued

```
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
    210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
        275                 280                 285

Arg Lys Arg Ala Thr Gly Ala Trp Ala Lys Leu Lys Glu Ser Arg Ala
    290                 295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Thr Asp Lys Gly Ala Gln Gln Pro Gly Trp Glu Glu
            340                 345                 350

Ser Asn His Pro Lys Tyr Asn
        355
```